(12) United States Patent
Fujimoto

(10) Patent No.: US 6,960,246 B2
(45) Date of Patent: Nov. 1, 2005

(54) OXYGEN CONCENTRATING APPARATUS

(75) Inventor: Naotoshi Fujimoto, Hino (JP)

(73) Assignee: Teijin Limited, Osaka (JP)

(*) Notice: Subject to any disclaimer, the term of this patent is extended or adjusted under 35 U.S.C. 154(b) by 7 days.

(21) Appl. No.: 10/466,612

(22) PCT Filed: Oct. 29, 2002

(86) PCT No.: PCT/JP02/11238
§ 371 (c)(1),
(2), (4) Date: Jul. 18, 2003

(87) PCT Pub. No.: WO03/037786
PCT Pub. Date: May 8, 2003

(65) Prior Publication Data
US 2004/0060445 A1 Apr. 1, 2004

(30) Foreign Application Priority Data
Oct. 30, 2001 (JP) .......................... 2001-332329
Nov. 6, 2001 (JP) .......................... 2001-340367

(51) Int. Cl.[7] .................................. B01D 53/047
(52) U.S. Cl. ......................... 96/110; 96/111; 96/112; 96/115; 96/130
(58) Field of Search ..................... 95/8, 11, 12, 14, 95/23, 130, 96–106; 96/110–112, 115, 130, 143, 144

(56) References Cited

U.S. PATENT DOCUMENTS

| | | | |
|---|---|---|---|
| 4,594,080 A | * | 6/1986 | Tremain et al. ............... 96/113 |
| 4,627,860 A | * | 12/1986 | Rowland ...................... 96/111 |
| 4,681,099 A | * | 7/1987 | Sato et al. ............. 128/204.23 |
| 4,783,205 A | * | 11/1988 | Searle ........................... 96/111 |
| 5,060,506 A | | 10/1991 | Douglas |
| 5,060,514 A | * | 10/1991 | Aylsworth .................. 73/24.01 |
| 5,071,453 A | * | 12/1991 | Hradek et al. ................ 96/111 |
| 5,247,826 A | * | 9/1993 | Frola et al. ................ 73/24.01 |
| 5,529,607 A | * | 6/1996 | Tan .............................. 95/12 |
| 5,531,807 A | * | 7/1996 | McCombs ..................... 95/26 |
| 5,593,478 A | * | 1/1997 | Hill et al. ..................... 96/111 |
| 5,627,323 A | * | 5/1997 | Stern ....................... 73/861.28 |
| 5,746,806 A | * | 5/1998 | Aylsworth et al. ............... 95/8 |
| 5,858,062 A | * | 1/1999 | McCulloh et al. ............... 95/8 |
| 5,906,672 A | * | 5/1999 | Michaels et al. ............. 95/12 |
| 5,917,135 A | * | 6/1999 | Michaels et al. ............. 95/11 |
| 6,063,169 A | * | 5/2000 | Cramer et al. ................ 96/112 |
| 6,342,090 B1 | * | 1/2002 | Cao ............................. 95/23 |
| 6,497,755 B2 | * | 12/2002 | Murdoch et al. ............. 96/110 |
| 6,712,876 B2 | * | 3/2004 | Cao et al. ...................... 95/10 |
| 2003/0136193 A1 | | 7/2003 | Fujimoto |

FOREIGN PATENT DOCUMENTS

| | | |
|---|---|---|
| JP | 06-213877 A1 | 8/1994 |
| JP | 2002-214012 A1 | 7/2002 |
| JP | 2002-214203 A1 | 7/2002 |
| WO | WO 02/57770 A1 | 7/2002 |

\* cited by examiner

Primary Examiner—Robert H. Spitzer
(74) Attorney, Agent, or Firm—Rader, Fishman & Grauer PLLC

(57) ABSTRACT

An apparatus for generating an oxygen enhanced gas by removing nitrogen gas from air, includes a compressor, absorption columns for removing the nitrogen gas from the pressurized air supplied from the compressor, a flow rate measuring device provided downstream of the absorption columns, a manner of measuring ultrasonic oxygen concentration that includes a manner of generating a correction coefficient for a ratio between oxygen and argon gases contained in the oxygen enhanced gas based on the flow rate of the oxygen enhanced gas measured.

8 Claims, 4 Drawing Sheets

Fig.1

OXYGEN ENHANCED GAS

OXYGEN CONCENTRATING APPARATUS

TECHNICAL FIELD

The invention relates to an oxygen concentrating apparatus for generating an oxygen enhanced gas for a medical purpose, and in particular to an oxygen concentrating apparatus improved to enable ultrasonic measurements of the oxygen concentration and/or the flow rate of the oxygen enhanced gas.

BACKGROUND ART

It is well known that the propagation velocity of ultrasonic waves through a sample gas is presented by a function of the concentration and the temperature of the sample gas. The velocity of ultrasonic waves C (m/sec) propagating through a sample gas is presented by following equation (1) with mean molecular weight M and the temperature T (K).

$$C=(\kappa RT/M)^{1/2} \qquad (1)$$

Where;
$\kappa$: ratio of molecular specific heat at constant volume and molecular specific heat at constant pressure
R: gas constant Therefore measuring the velocity of ultrasonic waves C (m/sec) propagating through a sample gas and the temperature T (K) of the sample gas will provide the mean molecular weight M of the sample gas through a calculation. For example, the mean molecular weight M of a sample gas containing an oxygen-nitrogen gas mixture of a mixture ratio P:(1−P)(0≦P≦1) will be calculated by M=$M_{O2}$P+$M_{N2}$(1−P), where $M_{O2}$: Molecular Weight of oxygen and $M_{N2}$: Molecular Weight of nitrogen. Therefore, the oxygen concentration P will be obtained through a calculation on the basis of the measurement of mean molecular weight M. When the sample gas is an oxygen-nitrogen mixture, $\kappa$=1.4 is reasonable over a wide range of the oxygen-nitrogen mixture ratio.

When the velocity of ultrasonic waves propagating through a sample gas is C (m/sec), and the flow velocity of the sample gas is V (m/sec), the velocity of ultrasonic waves $V_1$ (m/sec) propagating in the forward direction relative to the sample gas flow is $V_1$=C+V, and the velocity of ultrasonic waves $V_2$ (m/sec) propagating in the backward direction relative to the sample gas flow is $V_2$=C−V. Therefore, the velocity of the sample gas flow V (m/sec) is calculated by following equation (2).

$$V=(V_1-V_2)/2 \qquad (2)$$

The flow rate (m³/sec) of the sample gas will be obtained by multiplying this by the sectional area (m²) of the conduit through which the sample gas flows.

Methods and apparatuses for measuring the concentration of a certain gas or the flow velocity of a sample gas, using the above principle, on the basis of the propagation velocity or the propagation time of ultrasonic waves through the sample gas have been developed. For example, Japanese Unexamined Patent Publication (Kokai) No. 6-213877 describes an apparatus for measuring the concentration and the flow rate of a sample gas by measuring the propagation time of ultrasonic waves propagating between two ultrasonic transducers opposingly disposed in a conduit through which the sample gas flows. Further, Japanese Unexamined Patent Publications (Kokai) No. 7-209265 and No. 8-233718 describe an apparatus for measuring the concentration of a certain gas contained in a sample gas by measuring the propagation velocity or propagation time of ultrasonic waves propagating through a control volume with a reflecting type apparatus including an ultrasonic transducer and an opposingly disposed reflector. Further, U.S. Pat. No. 5,060,506 describes an apparatus for measuring the concentration of a two-component sample gas by measuring the changes in the velocity of ultrasonic waves.

Such a method and an apparatus for measuring the concentration and the flow rate by using the propagation velocity of the ultrasonic waves have problems. In the above-described method and apparatus, the sample gas includes only two components of oxygen gas and nitrogen gas. However, an oxygen concentrating apparatus actually outputs an oxygen enhanced gas including argon gas in addition to oxygen gas and nitrogen gas. Further, the concentration of argon gas is not constant and changes depending on the flow rate of the oxygen enhanced gas generated by the oxygen concentrating apparatus. Therefore, the conventional ultrasonic concentration measuring device cannot measure the concentration of oxygen gas accurately.

DISCLOSURE OF THE INVENTION

The invention is directed to solve the above-described problems of the prior art and to provide an oxygen concentrating apparatus improved to allow accurate ultrasonic measurements of the oxygen concentration if the flow rate of the oxygen enhanced gas generated by the oxygen concentrating apparatus changes.

According to the invention, there is provided an apparatus for generating an oxygen enhanced gas by removing nitrogen gas from air, comprising a pressurized air source, an absorption column for removing the nitrogen gas from the pressurized air supplied from the pressurized air source, a flow rate measuring device provided downstream of the absorption column, ultrasonic oxygen concentration measuring means provided downstream of the flow rate measuring device. The ultrasonic oxygen concentration measuring means comprises means for generating a correction coefficient for the ratio between oxygen and argon gases contained in the oxygen enhanced gas on the basis of the flow rate of the oxygen enhanced gas measured by the flow rate measuring device.

According to another feature of the invention, there is provided an apparatus for generating an oxygen enhanced gas by removing nitrogen gas from air, comprising a pressurized air source, an absorption column for removing the nitrogen gas from the pressurized air supplied from the pressurized air source, ultrasonic oxygen concentration and flow rate measuring means provided downstream of the flow rate setting device, and the ultrasonic oxygen concentration and flow rate measuring means comprising means for generating a correction coefficient for the ratio between oxygen and argon gases contained in the oxygen enhanced gas on the basis of the flow rate of the oxygen enhanced gas.

BEST MODE FOR CARRYING OUT THE INVENTION

Preferred embodiments of the invention will be described hereinafter.

Figure 1:
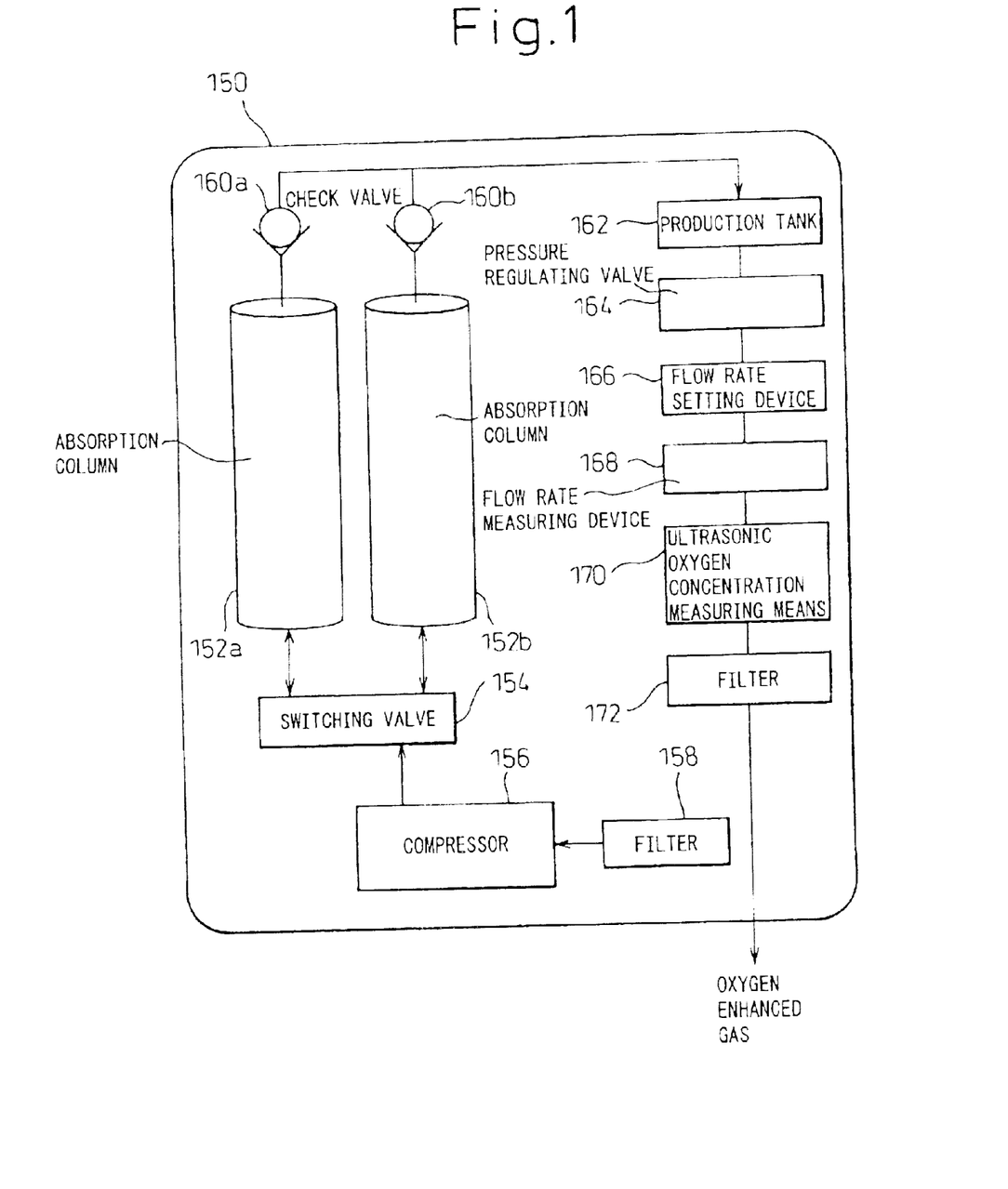
FIG. 1 is a block diagram of an oxygen concentrating apparatus according to a first embodiment of the invention.

With reference to FIG. 1, an oxygen concentrating apparatus 150 according to the invention is provided with two absorption columns 152a and 152b which are filled with a high performance Li-X type zeolite, a compressor 156, connected to the absorption columns 152a and 152b through a switching valve 154, for supplying compressed air to the absorption columns 152a and 152b and ultrasonic oxygen concentration measuring means 170 which is provided downstream of the absorption columns 152a and 152b.

The switching valve 154 selects one of the absorption columns 152a and 152b to fluidly connect it to the compressor 156. The air, drawn to the compressor 156 through a filter 158, is compressed by the compressor 156 and supplied to one of the absorption columns 152a and 152b, selected by the switching valve 154. The other of the absorption columns 152b and 152a, which is isolated from the compressor 156 by the switching valve 154, is opened to the atmosphere to release the absorbed nitrogen gas for the regeneration of the absorbent.

The oxygen enhanced gas, generated by removing nitrogen gas in the absorption columns 152a and 152b, is supplied to a production tank 162 through check valves 160a and 160b. From the production tank 162, the oxygen enhanced gas is supplied to a ultrasonic oxygen concentration measuring means 170 through a pressure regulating valve 164, a flow rate setting device 166 and a flow rate measuring device 168. After the oxygen concentration is measured, the oxygen enhanced gas is supplied to a user or a patient through a filter 172 for removing particles from the oxygen enhanced gas.

Figure 2:
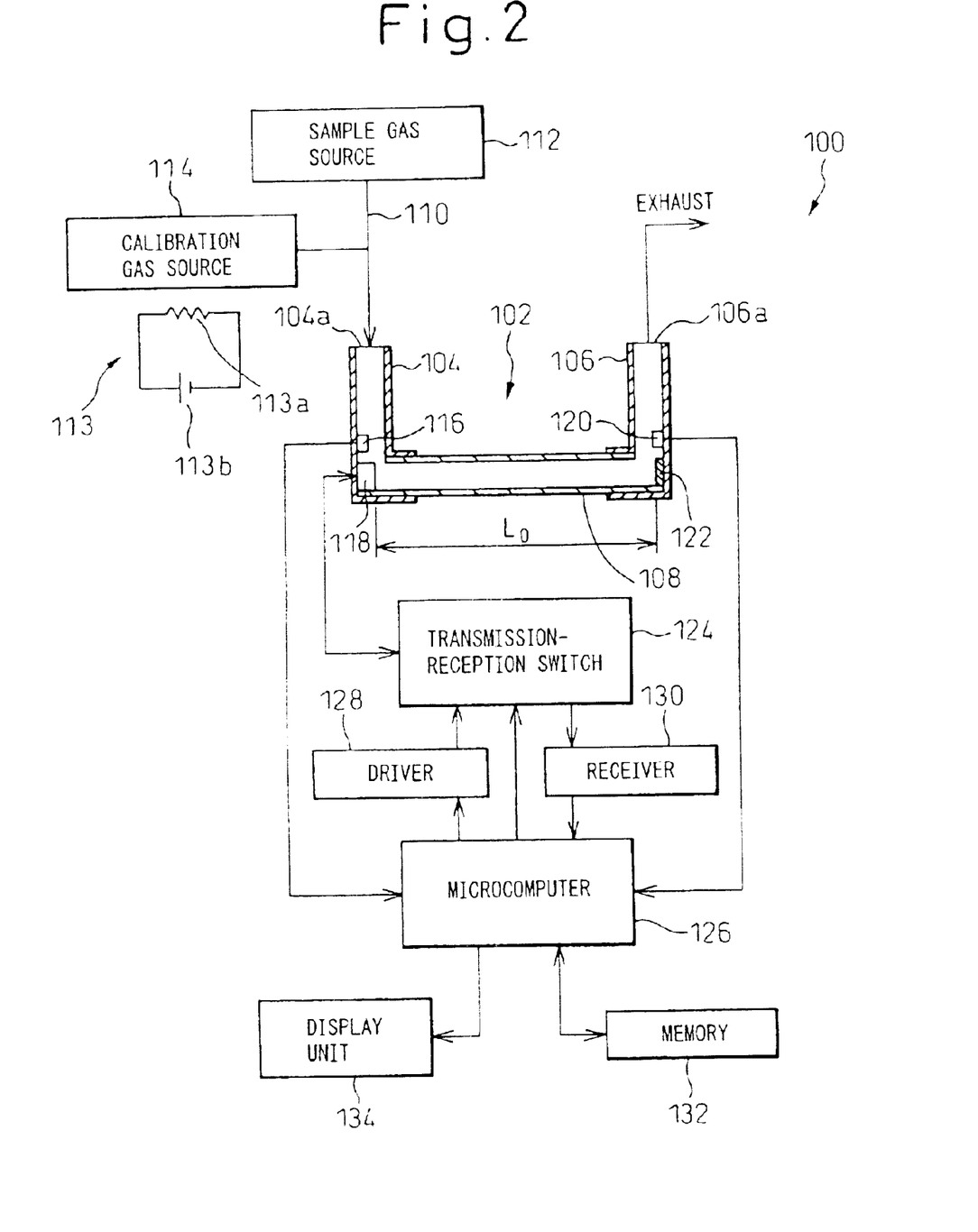
FIG. 2 is a schematic block diagram of an ultrasonic oxygen concentration measurement apparatus used in the oxygen concentrating apparatus of FIG. 1.

With reference to FIG. 2, a preferred embodiment of an ultrasonic oxygen concentration measuring device, which provides the ultrasonic oxygen concentration measuring means, will be described below.

The ultrasonic oxygen concentration measuring device 100 comprises a conduit 102 for flowing an oxygen enhanced gas or a calibration gas. The conduit 102 has a straight portion 108 and perpendicular portions 104 and 106 connected to the ends of the straight portion. An ultrasonic transducer 118 is fixedly provided at an end of the inside of the straight portion 108 as an ultrasonic transmission-reception device, and a reflector 122 is fixedly mounted to the other end of the inside of the straight portion 108 to face the ultrasonic transducer 118. In this embodiment, the distance between the ultrasonic transducer 118 and the reflector 122 is referred to as a test length.

A transmission-reception switch 124 is connected to the ultrasonic transducer 118. The transmission-reception switch 124 switches the operation mode of the ultrasonic transducer 118 between a transmission mode in which the ultrasonic transducer 118 transmits ultrasonic waves and a reception mode in which the ultrasonic transducer 118 receives the ultrasonic waves. The transmission-reception switch 124 is connected to a microcomputer 126 so that the switching operation of transmission-reception switch 124 is controlled by the microcomputer 126.

The perpendicular portion 104, disposed at the upstream side relative to the flow direction of the gas through the conduit 102, has an inlet port 104a. An oxygen enhanced gas source 112 and a calibration gas source 114 are connected to the inlet port 104a through a supply conduit 110. The oxygen enhanced gas source 112 includes the compressor 156, shown in FIG. 1, and absorption columns 152a and 152b.

The calibration gas source 114 may include a vessel (not shown) for containing a calibration gas, the component and the component ratio of which are known, for example, a gas mixture including 20% of oxygen and 80% of nitrogen, and a pressure reducing valve (not shown) provided between the vessel and the supply conduit 110.

The calibration gas source 114 may also include a temperature regulator 113, which provides means for changing the temperature of the device 100, in particular the conduit 102. In the example shown in FIG. 1, the temperature regulator 113 includes a heating wire 113a and an electric power source 113b for supplying the electric power to the heating wire 113a.

The perpendicular portion 106, disposed at the downstream side relative to the flow direction of the gas through the conduit 102, has an outlet port 106a. In the embodiment shown in FIG. 1, the filter 172 is connected to the outlet port 106a. The calibration gas used for the calibration is exhausted to the ambient air through the filter 172 or directly through the outlet port 106a.

Temperature sensors 116 and 120, for measuring the temperature of the oxygen enhanced gas or the calibration gas flowing through the conduit 102, are disposed preferably in the perpendicular portions 104 and 106 so that they do not disturb the flow in the straight portion 108. The temperature sensors 116 and 120 are connected to the microcomputer 126. In this connection, if the changes in the temperature of the oxygen enhanced gas is small, only one of the temperature sensors 116 or 120 may be disposed.

A driver 128 for driving the ultrasonic transducer 118, a receiver 130 for A/D conversion of the signals from the ultrasonic transducer 118, a display unit 134 for indicating, for example, the operating condition of the device 100 and the measurement results and memory 132 including a non-volatile memory device or a disc device for storing the operation system for the microcomputer 126 and various parameters are connected to the microcomputer 126.

The operation of the ultrasonic oxygen concentration measuring device will be described below.

First, prior to the initiation of the normal measuring process for measuring the concentration of a certain gas contained in the oxygen enhanced gas, the test length between the ultrasonic transmission-reception device 118 and the reflector 122 is calibrated, in accordance with the sequence described below, to obtain a reference length $L_0$.

A gas mixture, the component and the component ratio of which are known, for example an oxygen-nitrogen gas mixture of which mixture ratio is $P:(1-P)$ ($0 \leq P \leq 1$), is supplied to the conduit 102 as the calibration gas. At that time, the temperatures of the calibration gas are measured by the two temperature sensors 116 and 120 and the mean value thereof is stored in the memory 132 as a reference temperature $T_0$ (K). The reference temperature $T_0$ (K) may be any value which does not exceed the working temperature range of the device.

During the supply of the calibration gas, pulses for generating the ultrasonic waves are transmitted to the driver 128 from the microcomputer 126. A pulse voltage is supplied to the ultrasonic transducer 118 from the driver 128 through the transmission-reception switch 124. The ultrasonic transducer 118 generates ultrasonic waves corresponding to the pulse voltage. The ultrasonic waves generated by the ultrasonic transducer 118 propagate through the oxygen enhanced gas flowing through the straight portion 108 of the conduit 102 and are reflected by the reflector 122 to return to the ultrasonic transducer 118. In order to enable the ultrasonic transducer 118 to receive the returned ultrasonic waves, the transmission-reception switch 124 switches the operation mode of the ultrasonic transducer from the transmission mode to the reception mode right after the application of the pulse voltage to the ultrasonic transducer 118. The ultrasonic transducer 118 generates an electric signal corresponding to the received ultrasonic waves to the microcomputer 126 through the transmission-reception switch 124 and the receiver 130. The microcomputer 126 calculates the propagation time $t_0$ (sec) on the basis of the time when the transmitted pulses are generated to the first transducer 118 and the time when the electric signal is received from the ultrasonic transducer 118.

In this connection, the ultrasonic propagation velocity $C_0$ (m/sec) through the calibration gas at a temperature $T_0$ (K) is calculated by equation (3) on the basis of above-described equation (1).

$$C_0 = ((\kappa R T_0)/(M_{O2}P + M_{N2}(1-P)))^{1/2} \qquad (3)$$

On the other hand, the relation $$C_0 = 2L_0/t_0 \qquad (4)$$

gives the following equation.

$$L_0 = ((\kappa R T_0)/(M_{O2}P + M_{N2}(1-P)))^{1/2} \times t_0/2 \qquad (5)$$

Further, in the embodiment shown in FIG. 2, if the ultrasonic propagation velocity through a static calibration gas or oxygen enhanced gas is C (m/sec), and the flow velocity of the sample gas from the ultrasonic transducer 118 toward the reflector 122 is V (m/sec), then the ultrasonic propagation velocity from the ultrasonic transducer 118 to the reflector 122 is C+V and the ultrasonic propagation velocity in the direction of the ultrasonic waves reflected to the ultrasonic transducer 118 by the reflector 122 is C−V. Accordingly, the ultrasonic propagation velocity measured by the apparatus 100 of the first embodiment is the mean velocity of the reciprocating ultrasonic waves. Therefore, the flow velocity V of the sample gas is cancelled to allow the ultrasonic propagation velocity C through the static sample gas.

These calculations are conducted by the microcomputer 126. The test length $L_0$ (m) thus calculated at the reference temperature $T_0$ is stored in the memory 132 as the reference length.

The reference length $L_0$ (m) between the ultrasonic transducer 118 and the reflector 122 at the temperature $T_0$ (K) is calibrated according to the above method by supplying a calibration gas, the component and the component ratio of which is known, to the device 100 and measuring the propagation time t (sec) of the ultrasonic waves generated by the ultrasonic transducer 118. This calibration process can be automatically completed by the microcomputer 126 through a simple operation, for example one push of a button (not shown) provided on the device 100 when the calibration gas is supplied. Further, the process can be completed on the instant because the calculation itself is simple. Furthermore, if the relative position between the ultrasonic transducer 118 and the reflector 122 is changed due to the secular changes in the device 100, the device can be easily calibrated again to renew the reference temperature and the reference length stored in the memory 132.

As described above, the oxygen enhanced gas, output from the oxygen concentrating apparatus, includes argon gas in addition to oxygen and nitrogen gases. The argon concentration is not constant and changes with the flow rate of the oxygen enhanced gas produced by the oxygen concentrating apparatus.

Table 1 shows the result of gas component analysis in relation to the flow rate of the oxygen enhanced gas from the oxygen concentrating apparatus 150. The gas component analysis is conducted by gas chromatography.

TABLE 1

| Flow Rate (Liter/min) | Oxygen Concentration (%) | Argon Concentration (%) | Nitrogen Concentration (%) |
| --- | --- | --- | --- |
| 1.00 | 93.5 | 6.4 | 0.1 |
| 2.00 | 94.0 | 5.2 | 0.8 |
| 3.00 | 93.5 | 5.4 | 1.1 |

As shown in Table 1, the ratio between the oxygen, nitrogen and argon gases changes with the changes in the flow rate. In Table 1, the measurements were conducted with the oxygen enhanced gas generated by the oxygen concentrating apparatus 150. Although there are small differences, the oxygen/argon ratio is substantially the same when another similar type oxygen concentrating apparatus is used. On the other hand, the differences in the type and amount of the absorbent and the configuration of the absorption columns will result in the different oxygen/argon ratio.

Next, correction coefficient generating means for generating argon concentration correcting coefficient on the basis of the flow rate of the oxygen enhanced gas will be described below.

According to one method for correcting the argon concentration on the basis of the changes in the flow rate, the mean molecular weight M of equation (1) is directly described by using the abundance ratio between the oxygen and argon gases.

That is, on the assumption that the molecular weights of oxygen, nitrogen and argon gases are 32, 28 and 40, the mean molecular weight can be presented by following equation (6), when the output rate from the oxygen concentrating apparatus is 1.00 Liter/min.

$$M = 32P + 40(6.4/93.5)P + 28(1 - P - (6.4/93.5)P) \qquad (6)$$

Where, 100×P (%) is the oxygen concentration.

Further, the ratio of specific heat κ can be presented by following equation (7) by using the ratio of specific heat of the oxygen-nitrogen mixture 1.4 and that of argon gas 1.67.

$$\kappa = 1.4(1 - (6.4/93.5)P) + 1.67(6.4/93.5)P \qquad (7)$$

Thus, measurements of the propagation velocity of ultrasonic waves through the oxygen enhanced gas and the temperature of the gas will provide the oxygen concentration 100×P (%) on the basis of equations (1), (6) and (7).

In the above-described example, the flow rate of the oxygen enhanced gas is 1.00 Liter/min. In case of another value of the flow rate, (6.4/93.5) of the oxygen/argon ratio in equations (6) and (7) is replaced with another oxygen/argon ratio corresponding to the flow rate. In this case, the oxygen/argon ratio is the argon concentration correcting coefficient. Thus, the oxygen concentration can be accurately measured by obtaining the argon concentration correcting coefficient by referring a table on the basis of the oxygen enhanced gas flow rate. Further, the argon concentration correcting coefficient can be obtained as a function of the flow rate with an approximate equation by previously obtaining the relation between the measured flow rate and the oxygen/argon ratio.

In order to facilitate the calculation, the following method is also envisaged. First, the oxygen concentration is calculated by equation (2) with an assumption that the oxygen enhanced gas is composed of only oxygen and nitrogen gases. The oxygen concentration thus obtained is a value with the presence of argon gas neglected and, therefore, it is different from the actual value. However, the oxygen/argon ratio at a particular flow rate is previously known. Therefore, the oxygen concentration can be approximated by multiplying the previously calculated oxygen concentration by a factor. In this case, the factor provides the argon concentration correcting coefficient.

For example, when the flow rate of the oxygen enhanced gas is 1.00 Liter/min, 102.8 (%) of the oxygen concentration is calculated by equation (2) on the basis of the ratio of specific heat $\kappa=1.4$ and argon gas neglected. However, if 93.5 (%) of the actual oxygen concentration is previously known, (93.5/102.8) can be obtained as the argon concentration correcting coefficient at 1.00 Liter/min of the flow rate. Therefore, when the flow rate of the oxygen enhanced gas is 1.00 Liter/min, the oxygen concentration can be measured by multiplying the oxygen concentration, obtained by equation (2), by the argon concentration correcting coefficient (93.5/102.8).

If the flow rate is not 1.00 Liter/min, the oxygen concentration can be accurately measured by previously obtaining the argon concentration correcting coefficient in relation to the flow rate of the oxygen enhanced gas, and providing a table for referring the argon concentration correcting coefficient relative to the flow rate or an approximate equation of the argon concentration correcting coefficient in relation to the flow rate. The correction coefficient generating means can be realized by storing such a table or an approximate equation and the above-described algorithm for generating the correction coefficient in the memory 132 and conducting the same by the microprocessor 126.

Next, with reference to FIG. 3, a second embodiment of the invention will be described below.

The second embodiment is substantially the same as the first embodiment, except for that the flow rate measuring device 168 and the ultrasonic oxygen concentration measuring means 170 of the first embodiment are replaced with ultrasonic oxygen concentration and flow rate measuring means 268.

Figure 3:
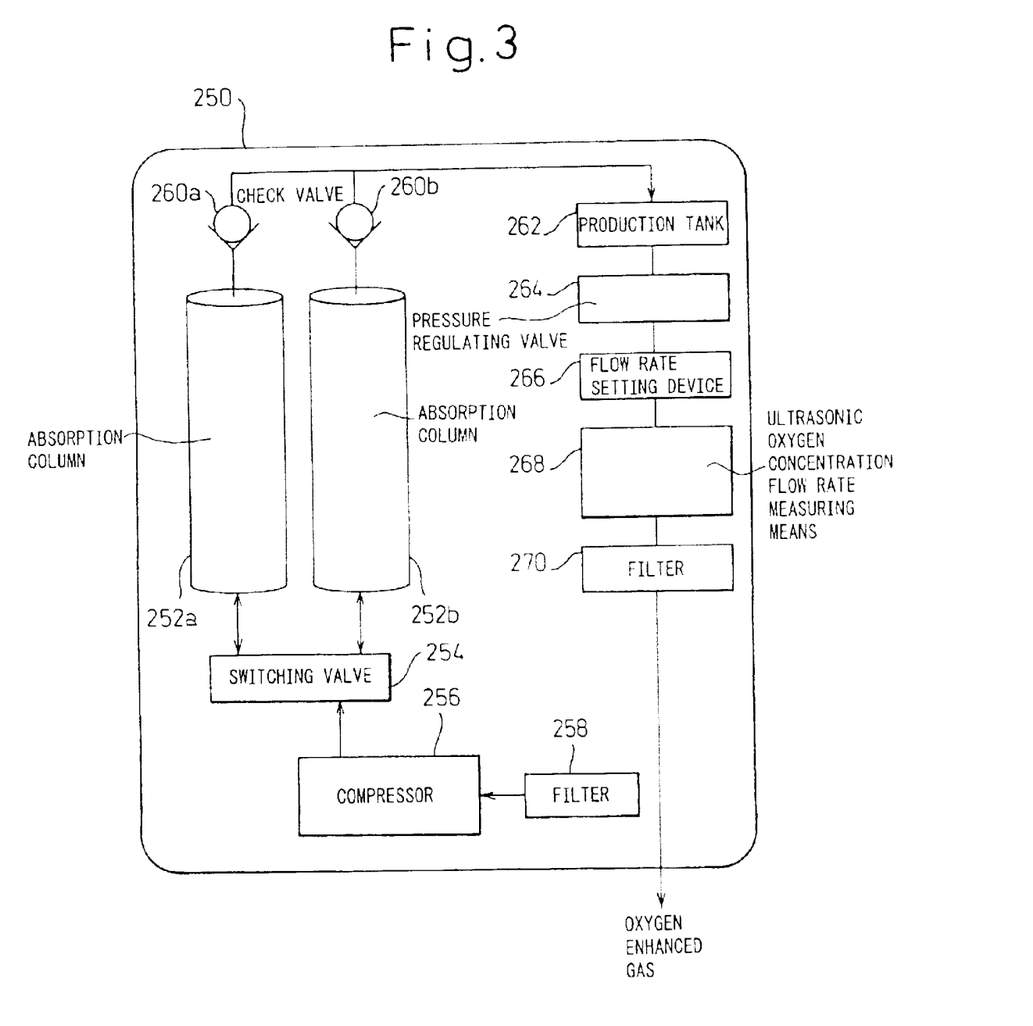
FIG. 3 is a block diagram of an oxygen concentrating apparatus according to a second embodiment of the invention.

With reference to FIG. 3, an oxygen concentrating apparatus 250 is provided with two absorption columns 252a and 252b which are filled with a high performance L±–X type zeolite, a compressor 256, connected to the absorption columns 252a and 252b through a switching valve 254, for supplying compressed air to the absorption columns 252a and 252b and ultrasonic oxygen concentration and flow rate measuring means 268 which is provided downstream of the absorption columns 252a and 252b.

The switching valve 254 selects one of the absorption columns 252a and 252b to fluidly connect it to the compressor 256. The air, drawn to the compressor 256 through a filter 258, is compressed by the compressor 256 and supplied to one of the absorption columns 252a and 252b, selected by the switching valve 254. The other of the absorption columns 252b and 252a, which is isolated from the compressor 256 by the switching valve 254, is opened to the atmosphere to release the absorbed nitrogen gas for the regeneration of the absorbent.

The oxygen enhanced gas, generated by removing nitrogen gas in the absorption columns 252a and 252b, is supplied to a production tank 262 through check valves 260a and 260b. From the production tank 262, the oxygen enhanced gas is supplied to an ultrasonic oxygen concentration and flow rate measuring means 268 through a pressure regulating valve 264 and a flow rate setting device 266. After the concentration and flow rate of the oxygen gas are measured, the oxygen enhanced gas is supplied to a user or a patient through a filter 270 for removing particles from the oxygen enhanced gas.

Next, with reference to FIG. 4, a preferred embodiment of an ultrasonic oxygen concentration and flow rate measuring device, which provides the ultrasonic oxygen concentration and flow rate measuring means 268, will be described below.

Figure 4:
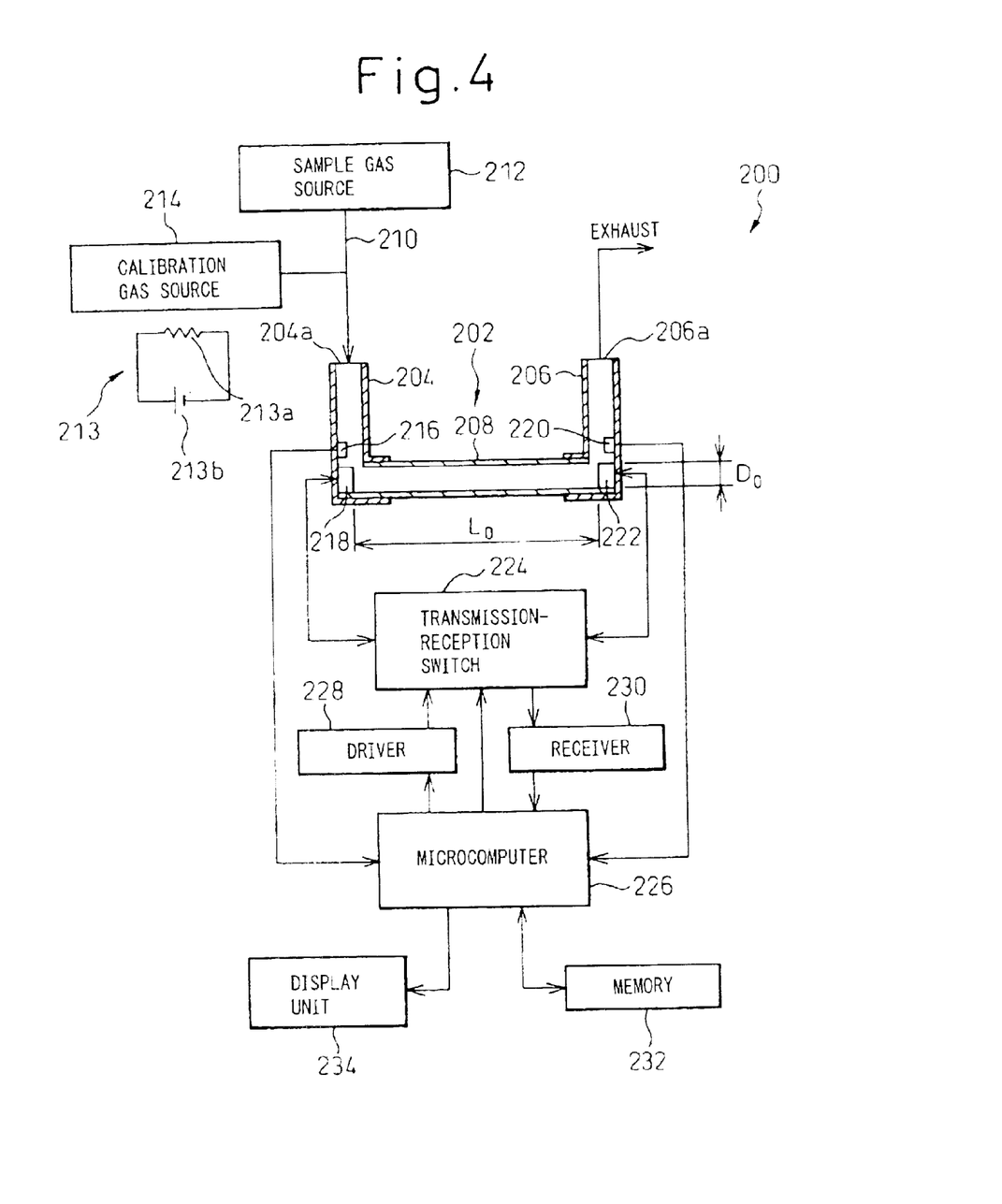
FIG. 4 is a schematic block diagram of an ultrasonic oxygen concentration and flow rate measurement apparatus used in the oxygen concentrating apparatus of FIG. 3.

The embodiment shown in FIG. 4 has substantially the same configuration of the embodiment shown in FIG. 2, except for that the reflector 122 of the embodiment shown in FIG. 2 is replaced with a second ultrasonic transducer 222, which provides a second ultrasonic transmission-reception device, disposed to face a first ultrasonic transducer 218, which provides a first ultrasonic transmission-reception device.

An ultrasonic gas concentration and flow rate measuring device 200 according to the embodiment shown in FIG. 4 includes a conduit 202 for flowing an oxygen enhanced gas or a calibration gas. The conduit 202 has a straight portion 208 and perpendicular portions 204 and 206 connected to the ends of the straight portion. The straight portion 208 comprises, in this embodiment, a conduit member having a circular section, the diameter of which, does not change along the longitudinal axis. A first ultrasonic transducer 218, providing a first ultrasonic transmission-reception device, is fixedly provided at the upstream end of the inside of the straight portion, and a second ultrasonic transducer 222, providing a second ultrasonic transmission-reception device, is fixedly mounted to the downstream end of the inside of the straight portion 208 to face the first ultrasonic transducer 218. In this embodiment, the distance between the first and second ultrasonic transducers 218 and 222 is referred to as a test length.

A transmission-reception switch 224 is connected to the first and second ultrasonic transducers 218 and 222. The transmission-reception switch 224 independently switches the operation mode of the first and second ultrasonic transducers 218 and 222 between a transmission mode in which the first and second ultrasonic transducers 218 and 222 transmit ultrasonic waves and a reception mode in which the first and second ultrasonic transducers 218 and 222 receive the ultrasonic waves. The transmission-reception switch 224 is connected to a microcomputer 226 so that the switching operation of transmission-reception switch 224 is controlled by the microcomputer 226.

The upstream side perpendicular portion 204 of the conduit 202 has an inlet port 204a. An oxygen enhanced gas source 212 and a calibration gas source 214 are connected to the inlet port 204a through a supply conduit 210. The oxygen enhanced gas source 212 includes the compressor 256 and the absorption columns 252a and 252b shown in FIG. 3.

The calibration gas source 214 may include a vessel (not shown) for containing a calibration gas, the component and the component ratio of which are known, and a pressure reducing valve (not shown) provided between the vessel and the supply conduit 210. The calibration gas source 214 may also include a temperature regulator 213, which provides means for changing the temperature of the device 200, in particular the conduit 202. In the example shown in FIG. 4, the temperature regulator 213 includes a heating wire 213a and an electric power source 213b for supplying the electric power to the heating wire 213a.

The downstream side perpendicular portion 206 has an outlet port 206a. The oxygen enhanced gas or the calibration gas used for the concentration measurement or the calibration is exhausted through the outlet port 206a. A gas processing apparatus (not shown) may advantageously be disposed downstream of the outlet port 206a if the exhausted gas is not suitable to directly exhaust to the atmosphere, as in the first embodiment.

Temperature sensors 216 and 220, for measuring the temperature of the oxygen enhanced gas or the calibration gas flowing through the conduit 202, are disposed preferably in the perpendicular portions 204 and 206 so that they do not disturb the flow in the straight portion 208. The temperature sensors 216 and 220 are connected to the microcomputer 226. In this connection, if the changes in the temperature of the oxygen enhanced gas is small, only one of the temperature sensors 216 or 220 may be disposed.

A driver 228 for driving the first ultrasonic transducer 218, a receiver 230 for A/D conversion of the signals from the first ultrasonic transducer 218, a display unit 234 for indicating, for example, the operating condition of the device 200 and the measurement results and memory 232 including a nonvolatile memory device or a disc device for storing the operation system for the microcomputer 226 and various parameters are connected to the microcomputer 226.

The operation of the embodiment shown in FIG. 4 will be described below.

First, prior to the initiation of the normal measuring process for measuring the concentration of a certain gas contained in the oxygen enhanced gas, the test length between the first and second ultrasonic transducers 218 and 222 and the diameter D of the straight portion 208 of the conduit 202 are calibrated to obtain the reference length $L_0$ and the reference diameter $D_0$.

In the present embodiment, the calibration gas, identical to that in the first embodiment, is supplied to the conduit 202 from the calibration gas source 214 at a predetermined rate $Q_0$ by the flow regulating valve. At that time, the temperatures of the calibration gas are measured by the two temperature sensors 216 and 220 and the mean value thereof is stored in the memory 232 as a reference temperature $T_0$ (K).

During the supply of the calibration gas, pulses for generating the ultrasonic waves are transmitted to the driver 228 from the microcomputer 226. A pulse voltage is supplied to the first ultrasonic transducer 218 from the driver 228 through the transmission-reception switch 224. The first ultrasonic transducer 218 generates ultrasonic waves corresponding to the pulse voltage. The ultrasonic waves generated by the first ultrasonic transducer 218 propagate through the oxygen enhanced gas flowing through the straight portion 208 of the conduit 202 and are received by the second ultrasonic transducer 222. The second ultrasonic transducer 222 generates an electric signal corresponding to the received ultrasonic waves to the microcomputer 226 through the transmission-reception switch 224 and the receiver 230. The microcomputer 226 calculates the forward propagation time $t_1$ (sec) on the basis of the time when the transmitted pulses are generated to the driver 228 and the time when the electric signal is received from the second ultrasonic transducer 222.

The transmission-reception switch 224 switches the operation mode of the first ultrasonic transducer 218 from the transmission mode to the reception mode right after the electric signal from the second ultrasonic transducer 222 is received and also switches the operation mode of the second ultrasonic transducer 222 from the reception mode to the transmission mode. Thereafter, pulses for generating the ultrasonic waves are transmitted to the driver 228 from the microcomputer 226. A pulse voltage is supplied to the second ultrasonic transducer 222 from the driver 228 through the transmission-reception switch 224. The second ultrasonic transducer 222 generates ultrasonic waves corresponding to the pulse voltage. The ultrasonic waves are received by the first ultrasonic transducer 218. The first ultrasonic transducer 218 generates an electric signal corresponding to the received ultrasonic waves to the microcomputer 226 through the transmission-reception switch 224 and the receiver 230. The microcomputer 226 calculates the backward propagation time $t_2$ (sec) on the basis of the time when the transmitted pulses are generated to the driver 228 and the time when the electric signal is received from the first ultrasonic transducer 218.

By obtaining the mean value of $t_1$ and $t_2$, the affection of the flow of the calibration gas in the conduit 202 can be removed. The ultrasonic propagation time $t_0$ is defined by following equation (8).

$$t_0=(t_1+t_2)/2 \qquad (8)$$

In this connection, the ultrasonic propagation velocity $C_0$ (m/sec) through the gas at a temperature $T_0$ (K) is calculated by the above-described equation (3).

On the other hand, the relation $$C_0=L_0/t_0 \qquad (9)$$

gives the following equation.

$$L_0=((\kappa RT_0)/(M_{O2}P+M_{N2}(1-P)))^{1/2} \times t_0 \qquad (10)$$

These calculations are conducted by the microcomputer 226. The test length $L_0$ (m) thus calculated at the reference temperature $T_0$ is stored in the memory 232 as the reference length.

Further, by using this reference length $L_0$, the forward propagation velocity $V_{01}$ (m/sec) and the backward propagation velocity $V_{02}$ (m/sec), relative to the flow direction of the calibration gas, are represented by $V_{01}=L_0/t_1$ and $V_{02}=L_0/t_2$. Therefore, the flow velocity $V_0$ (m/sec) of the calibration gas in the conduit 202 is obtained by following equation (11), on the basis of above-described equation (2).

$$V_0=(V_{01}-V_{02})/2 \qquad (11)$$

Multiplication of the flow velocity V by the sectional area ($m^2$) of the straight portion 208, perpendicular to the axis of the straight portion 208 of the conduit 202, gives a conversion of the flow velocity (m/sec) to the flow rate ($m^3$/sec). Thus, the reference diameter $D_0$ (m) at the reference temperature $T_0$ (K) of the straight portion 208 gives the following equation.

$$V_0 \pi (D_0/2)^2=Q_0 \qquad (12)$$

Therefore, the reference diameter $D_0$ (m) at the reference temperature $T_0$ (K) can be obtained by following equation (13):

$$D_0=2(Q_0/(\pi V_0))^{1/2} \qquad (13)$$

The above calculation is conducted by the microcomputer 226, and the reference diameter $D_0$ (m) thus obtained is stored in the memory 232.

According to the above method, the reference length $L_0$ (in) between the first and second ultrasonic transducers 218 and 222 is calibrated at a temperature $T_0$ (K) by supplying a calibration gas, the component and the concentration of which is known, to the device 200, and measuring the propagation times $t_1$ and $t_2$ in the forward and backward directions relative to the flow of the calibration gas, from the first and second ultrasonic transducers 218 and 222. Additionally, by supplying the calibration gas to the device 200 at a predetermined rate, the reference diameter $D_0$ (m) can also be calibrated at the same time.

According to the first embodiment, the oxygen concentration correcting coefficient is generated on the basis of the flow rate of the oxygen enhanced gas measured by the flow rate measuring device 168. On the other hand, according to the second embodiment, the oxygen concentration correcting coefficient is calculated on the basis of the flow rate of the oxygen enhanced gas measured by the ultrasonic oxygen concentration and flow rate measuring device 200. The other functions are the same as the first embodiment.

What is claimed is:

1. An apparatus for generating an oxygen enhanced gas by removing nitrogen gas from pressurized air, comprising:

a pressurized air source;

an absorption column for removing the nitrogen gas from the pressurized air supplied from the pressurized air source;

ultrasonic oxygen concentration measuring means provided downstream of the absorption column, wherein the ultrasonic oxygen concentration measuring means comprises means for generating a correction coefficient for a ratio between oxygen and argon gases contained in the oxygen enhanced gas based on a flow rate of the oxygen enhanced gas measured by a flow rate measuring device.

2. The apparatus according to claim 1, wherein the ultrasonic oxygen concentration measuring means comprises:

a conduit for flowing an objective gas the concentration of which is measured;

an ultrasonic transmission-reception device secured inside of the conduit;

a reflector secured inside of the conduit to face the ultrasonic transmission-reception device;

a transmission-reception switch for switching the operation mode of the ultrasonic transmission-reception device between a transmission mode in which the ultrasonic transmission-reception device transmits ultrasonic waves and a reception mode in which the ultrasonic transmission-reception device receives the ultrasonic waves;

a temperature sensor, disposed inside of the conduit, for measuring the temperature of a calibration gas flowing through the conduit;

propagation time calculating means for calculating a propagation time of ultrasonic waves through the calibration gas within the conduit based on when the ultrasonic waves are transmitted by the ultrasonic transmission-reception device and when the ultrasonic waves reflected by the reflector are received by the ultrasonic transmission-reception device;

and means for generating a correction coefficient for the ratio between oxygen and argon gases contained in the oxygen enhanced gas based on the flow rate of the oxygen enhanced gas measured by the flow rate measuring device wherein the oxygen concentration of the oxygen enhanced gas is corrected based on the correction coefficient generated by the correction coefficient generating means.

3. The apparatus according to claim 2, wherein the ultrasonic oxygen concentration measuring means comprises a calibration gas source for supplying the calibration gas the component and the component ratio of which is known; and means for calibrating a reference length between the ultrasonic transmission-reception device and the reflector based on the calculation of the propagation time calculating means when the calibration gas flows through the conduit from the calibration gas source.

4. The apparatus according to claim 1, further comprising:

a conduit for flowing an objective gas the concentration of which is measured;

an ultrasonic transmission-reception device secured inside of the conduit;

a reflector secured inside of the conduit to face the ultrasonic transmission-reception device; and propagation time calculating means for calculating the propagation time of ultrasonic waves through a calibration gas within the conduit on the basis of the time when the ultrasonic waves are transmitted by the ultrasonic transmission-reception device and the time when the ultrasonic waves reflected by the reflector are received by the ultrasonic transmission-reception device, wherein the ultrasonic oxygen concentration measuring means comprises a calibration gas source for supplying the calibration gas, predetermined component gases, and a predetermined component ratio; and means for calibrating a reference length between the ultrasonic transmission-reception device and the reflector based on calculation results of the propagation time calculating means when the calibration gas flows through the conduit from the calibration gas source.

5. An apparatus for generating an oxygen enhanced gas by removing nitrogen gas from pressurized air, comprising:

a pressurized air source;

an absorption column for removing the nitrogen gas from the pressurized air supplied from the pressurized air source;

ultrasonic oxygen concentration and flow rate measuring means provided downstream of the absorption column, wherein the ultrasonic oxygen concentration and flow rate measuring means comprises means for generating a correction coefficient for a ratio between oxygen and argon gases contained in the oxygen enhanced gas based on a flow rate of the oxygen enhanced gas measured by the ultrasonic oxygen concentration and flow rate measuring means.

6. The apparatus according to claim 5, wherein the ultrasonic oxygen concentration and flow rate measuring means comprises:

a conduit for flowing an objective gas the concentration of which is measured;

a first ultrasonic transmission-reception device secured inside of the conduit;

a second ultrasonic transmission-reception device secured inside of the conduit to face the first ultrasonic transmission-reception device;

a transmission-reception switch for switching the operation mode of each of the first and second ultrasonic transmission-reception devices between a transmission mode in which the ultrasonic transmission-reception device transmits ultrasonic waves and a reception mode in which the ultrasonic transmission-reception device receives the ultrasonic waves;

a temperature sensor, disposed inside of the conduit, for measuring the temperature of a calibration gas flowing through the conduit; and propagation time calculating means for calculating a first propagation time of ultrasonic waves through the calibration gas within the conduit based on when the ultrasonic waves are transmitted by the first ultrasonic transmission-reception device and when the ultrasonic waves are received by the second ultrasonic transmission-reception device, and for calculating a second propagation time of ultrasonic waves though the calibration gas within the conduit based on when the ultrasonic waves are transmitted by the second ultrasonic transmission-reception device and when the ultrasonic waves are received by the first ultrasonic transmission-reception device.

7. The apparatus according to claim 6, wherein the ultrasonic oxygen concentration and flow rate measuring means comprises a calibration gas source for supplying the calibration gas the component, the component ratio and the flow rate of which are known;

means for calibrating a reference length between the first and second ultrasonic transmission-reception devices on the basis of the calculation results by the propagation time calculating means when the calibration gas flows through the conduit from the calibration gas source;

means for calibrating a reference diameter of the conduit; and means for generating a correction coefficient for the ratio between oxygen and argon gases contained in the oxygen enhanced gas based on the flow rate of the oxygen enhanced gas wherein the oxygen concentration of the oxygen enhanced gas is corrected based on the correction coefficient generated by the correction coefficient generating means.

8. The apparatus according to claim 5, further comprising:

a conduit for flowing an objective gas the concentration of which is measured;

a first ultrasonic transmission-reception device secured inside of the conduit;

a second ultrasonic transmission-reception device secured inside of the conduit to face the first ultrasonic transmission-reception device; and propagation time calculating means for calculating first propagation time of ultrasonic waves through a calibration gas within the conduit on the basis of the time when the ultrasonic waves are transmitted by the first ultrasonic transmission-reception device and the time when the ultrasonic waves are received by the second ultrasonic transmission-reception device, and for calculating second propagation time of ultrasonic waves through the calibration gas within the conduit on the basis of the time when the ultrasonic waves are transmitted by the second ultrasonic transmission-reception device and the time when the ultrasonic waves are received by the first ultrasonic transmission-reception device, wherein the ultrasonic oxygen concentration and flow rate measuring means comprises:

a calibration gas source for supplying the calibration gas, predetermined component gases, a predetermined component ratio, and the flow rate;

means for calibrating a reference length between the first and second ultrasonic transmission-reception devices based on the calculation of the propagation time calculating means when the calibration gas flows through the conduit from the calibration gas source;

means for calibrating a reference diameter of the conduit; and means for generating the correction coefficient for the ratio between oxygen and argon gases contained in the oxygen enhanced gas based on the flow rate of the oxygen enhanced gas wherein the oxygen concentration of the oxygen enhanced gas is corrected based on the correction coefficient generated by the correction coefficient generating means.

* * * * *